United States Patent
Hupke

Patent Number: 5,867,554
Date of Patent: Feb. 2, 1999

[54] SPIRAL SCAN COMPUTED TOMOGRAPHY APPARATUS HAVING A MODULAR SURFACE DETECTOR FOR RADIATION

[75] Inventor: Rolf Hupke, Eckental, Germany

[73] Assignee: Siemens Aktiengesellschaft, Munich, Germany

[21] Appl. No.: 862,316

[22] Filed: May 23, 1997

[30] Foreign Application Priority Data

Jun. 20, 1996 [DE] Germany ............... 196 24 681.4

[51] Int. Cl.$^6$ ........................................ A61B 6/03
[52] U.S. Cl. ............................... 378/4; 378/19
[58] Field of Search ................... 378/4, 19, 98.8

[56] References Cited

U.S. PATENT DOCUMENTS 5,164,583 11/1992 Aichinger .
5,241,576 8/1993 Lonn ................................ 378/19
5,291,402 3/1994 Pfoh .
5,430,784 7/1995 Ribner et al. ..................... 378/19
5,448,613 9/1995 Haendle et al. .
5,579,359 11/1996 Toth ................................ 378/19
5,583,903 12/1996 Saito et al. ...................... 378/19
5,737,382 4/1998 Stierstorfer ...................... 378/19

*Primary Examiner*—David P. Porta
*Attorney, Agent, or Firm*—Hill & Simpson

[57] ABSTRACT

A computed tomography apparatus has a radiation detector formed by several parallel detector rows of detector elements. A flexible selection of slices is enabled with a simple construction by constructing the detector from a series of detector modules. Each detector module is formed by several parallel sub-modules, and each sub-module is formed by a series of detector elements. The series of detector elements can be formed by slits in the module. Each detector element is constructed on the basis of a ceramic scintillator with a subsequently connected photodetector.

6 Claims, 3 Drawing Sheets

SPIRAL SCAN COMPUTED TOMOGRAPHY APPARATUS HAVING A MODULAR SURFACE DETECTOR FOR RADIATION

BACKGROUND OF THE INVENTION

1. Field of the Invention

The present invention is directed to a computed tomography apparatus of the type employing a surface detector for detecting radiation attenuated by an examination subject during the course of a spiral scan.

2. Description of the Prior Art

In computed tomography systems currently used in medical technology, the projection data required for a sectional image are exposed by passing the entire beam "bundle" from the X-ray source through one or more diaphragms so that only a thin fan beam remains, and detecting the radiation from this fan beam which is transmitted through the subject using a single detector row. The length of the individual detector elements in the z-direction (direction of the system axis) is dimensioned so that the detector elements can fully receive the radiation for the largest slice thickness that can be set (a 10 mm slice is standard).

Different slice thicknesses are produced by means of corresponding settings of the diaphragm near the tube and a diaphragm at the detector side. With an arrangement of this sort only the data for one slice can be recorded, and thus the X-ray radiation emitted by the X-ray source is used very inefficiently. For three-dimensional exposure techniques, the volume that can be acquired is generally limited by the available continuous power of the X-ray source. The required exposure times, or examination times thus are correspondingly long.

Limitations of this sort in the measurement system are largely overcome if, according to U.S. Pat. No. 5,291,402, a surface detector is used. A surface detector of this sort is a two-dimensional array of detector elements (mosaic), i.e. it is formed from several parallel detector rows, so that, in place of a thin fan beam, an X-ray beam bundle that is also extended in the z-direction can be used for imaging. In contrast to a conventional single-row detector, a surface detector also contains detector elements that are spatially separated in the z-direction. Given a rotation of the measurement system, this allows many slices to be exposed simultaneously, depending on the extension of the surface detector in the z-direction. Adjacent rows of the surface detector thereby acquire adjacent slices. The length of the detector elements in the z-direction for this type of detector thus is chosen so that a detector row acquires the smallest desired slice.

SUMMARY OF THE INVENTION

An object of the present invention is to provide a computed tomography apparatus having a surface detector wherein a simple detector construction and a variable slice selection are enabled.

It is important in the context of the invention that the detector is constructed from modules, preferably based on a detector ceramic, these modules being structured in the φ-direction according to requirements, i.e. in the direction of the rotation of the measurement arrangement of the X-ray source and detector.

DESCRIPTION OF THE PREFERRED EMBODIMENTS

Figure 1:
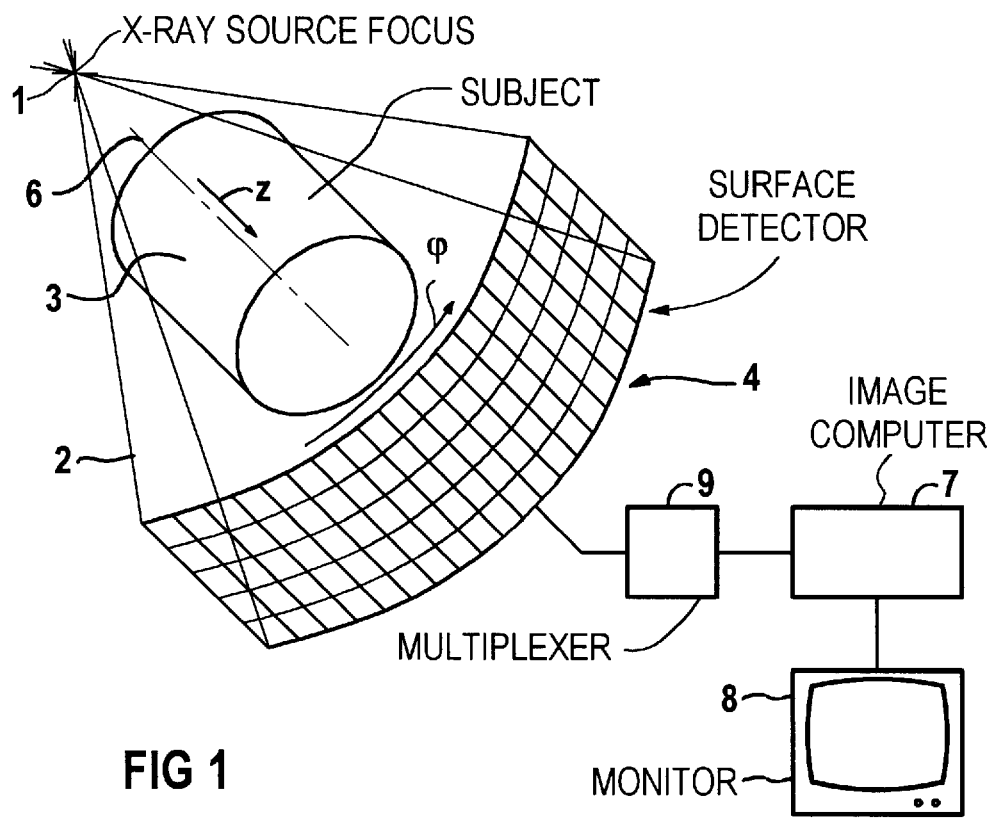
FIG. 1 shows the basic components of a computed tomography apparatus, for explaining the invention.

FIG. 1 shows the focus 1 of an X-ray source, from which a fan-shaped X-ray beam bundle (pyramidal beam) 2, emanates screened by means of a diaphragm arrangement (not shown). The bundle 2 penetrates a subject 3 and strikes a detector 4 composed of several parallel detector rows, each row being formed from a series of detector elements. The measurement system, composed of the detector 4 and (at least) the focus 1 of the X-ray source, can be rotated about a system axis 6 in the (φ-direction, so that the subject 3 is transirradiated from various projection angles (axial mode and spiral mode). From the detector signals that are thereby formed, a computer 7 forms an image of the subject 3 corresponding to the slice thickness (which is adjustable) that has been set. The image is reproduced on a monitor 8. The acquisition of the detector signals ensues by means of a multiplexer 9.

Figure 2:
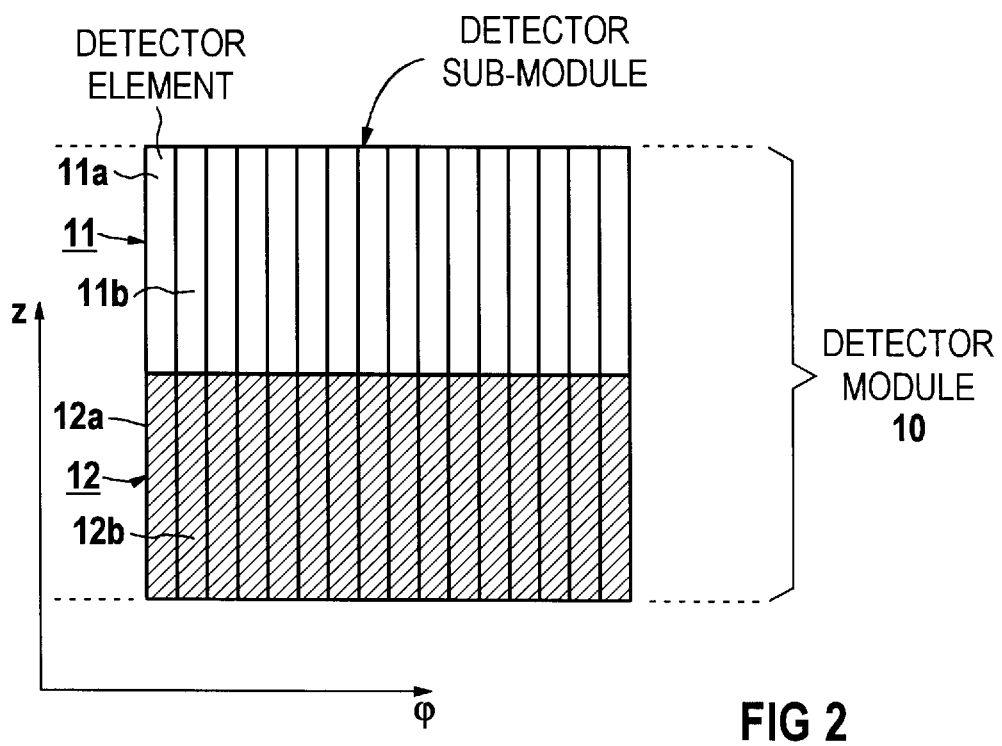
FIGS. 2 through 6 respectively show various embodiments of detector constructions and detector screenings for producing various numbers of slices and various slice thicknesses in accordance with the principles of the present invention.

The detector 4 is constructed from a series of modules that preferably each contain a series of ceramic scintillators with subsequently connected photodiodes. FIG. 2 shows an embodiment with a module 10 that is slit into sixteen elements in the φ-direction and into two sub-modules 11 and 12 in the z-direction. Each sub-module 11 and 12 is accordingly partitioned into a series of detector elements 11a, 11b, etc., or 12a, 12b, etc. In the (φ-direction, a number of modules are connected to one another in a series, corresponding to the module 10. It is thus possible to scan simultaneously two parallel slices that extend in the z-direction.

Figure 3:
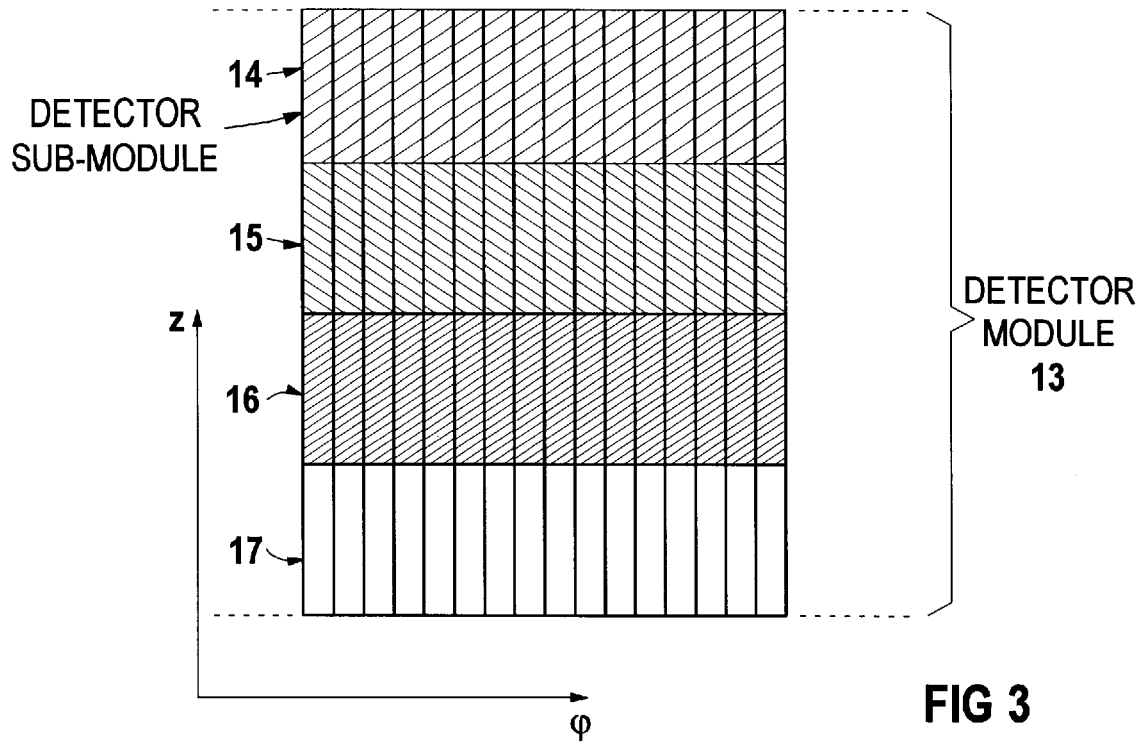

FIG. 3 shows the construction of a detector from modules 13, whereby each module 13 is constructed from four parallel sub-modules 14 to 17. The sub-modules 14 to 17 are slit in the φ-direction likewise into, e.g., sixteen elements. It is thereby possible to scan simultaneously four parallel slices extending in the z-direction.

Figure 4:
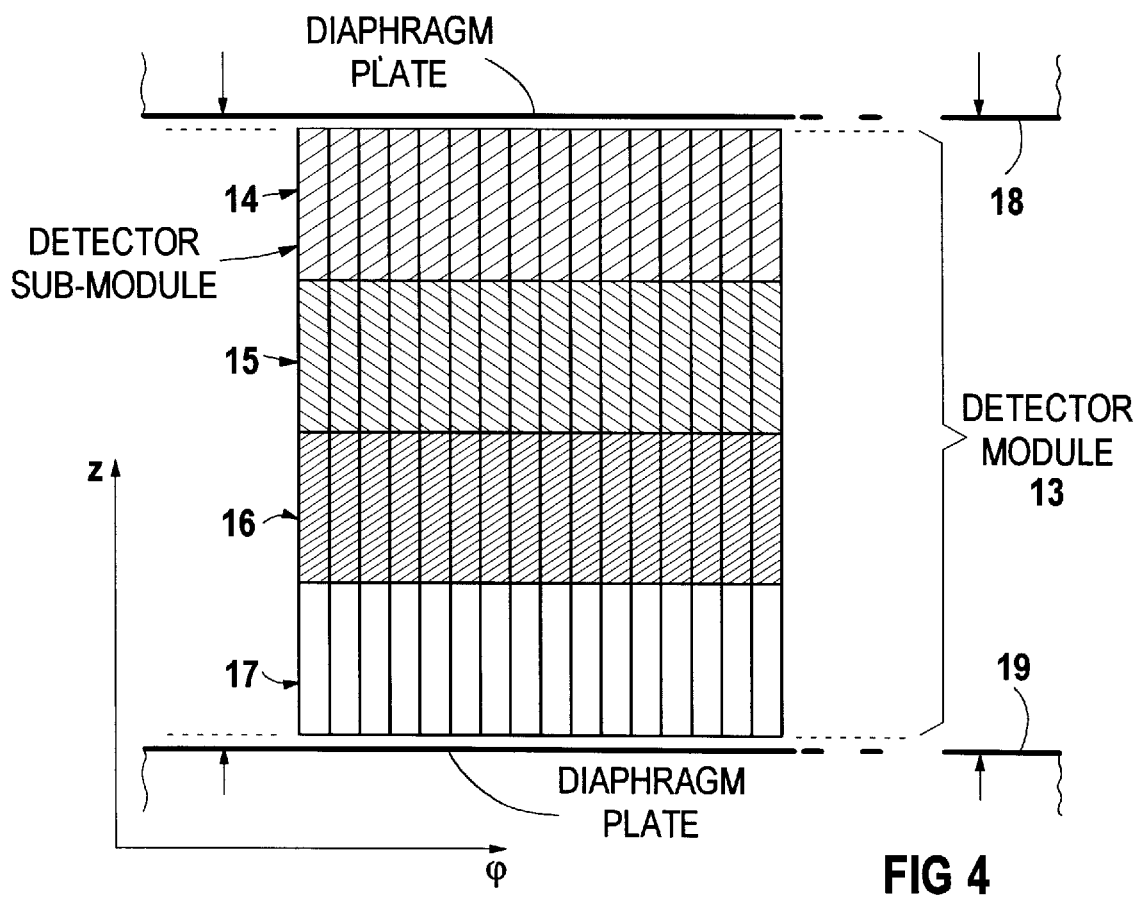

FIG. 4 shows a detector construction corresponding to FIG. 3, with associated diaphragm plates 18 and 19 near the detector. Corresponding to the position of the diaphragm plates 18 and 19, all four parallel detector rows respectively forming the sub-modules 14 to 17 are active, and four slices can be scanned simultaneously. If the signals of detector elements which correspond to one another in the respective sub-modules 14 and 15 are combined, and the same is done for corresponding detector elements in the respective sub-module 16 and 17, then two parallel detector rows of the sub-modules 14 and 15, and two parallel detector rows of the sub-modules 16 and 17, respectively supply the signals for a slice, so that two parallel slices can be scanned simultaneously.

Figure 5:
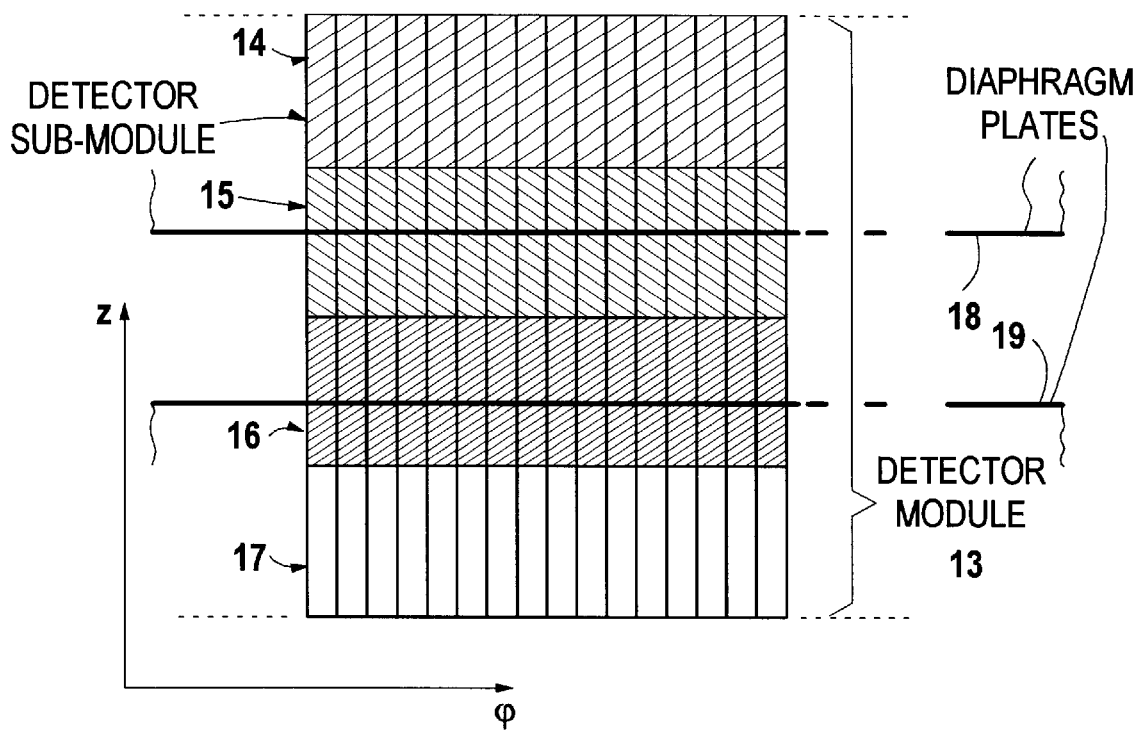

FIG. 5 shows the detector according to FIGS. 3 and 4, with the diaphragm plates 18 and 19 positioned for scanning two parallel slices, that are defined by the sub-modules 15 and 16. The sub-modules 14 and 17 are inactive. The sub-modules 15 and 16 are partly covered by the diaphragm plates 18 and 19, so that a smaller slice thickness results than would be possible if the full dimensions of the sub-modules 15 and 16 were used.

With the diaphragm position according to FIG. 4, for example four slices with thickness 5 mm can be scanned, while with the diaphragm position according to FIG. 5, two slices of 3 mm thickness can be scanned.

Figure 6:
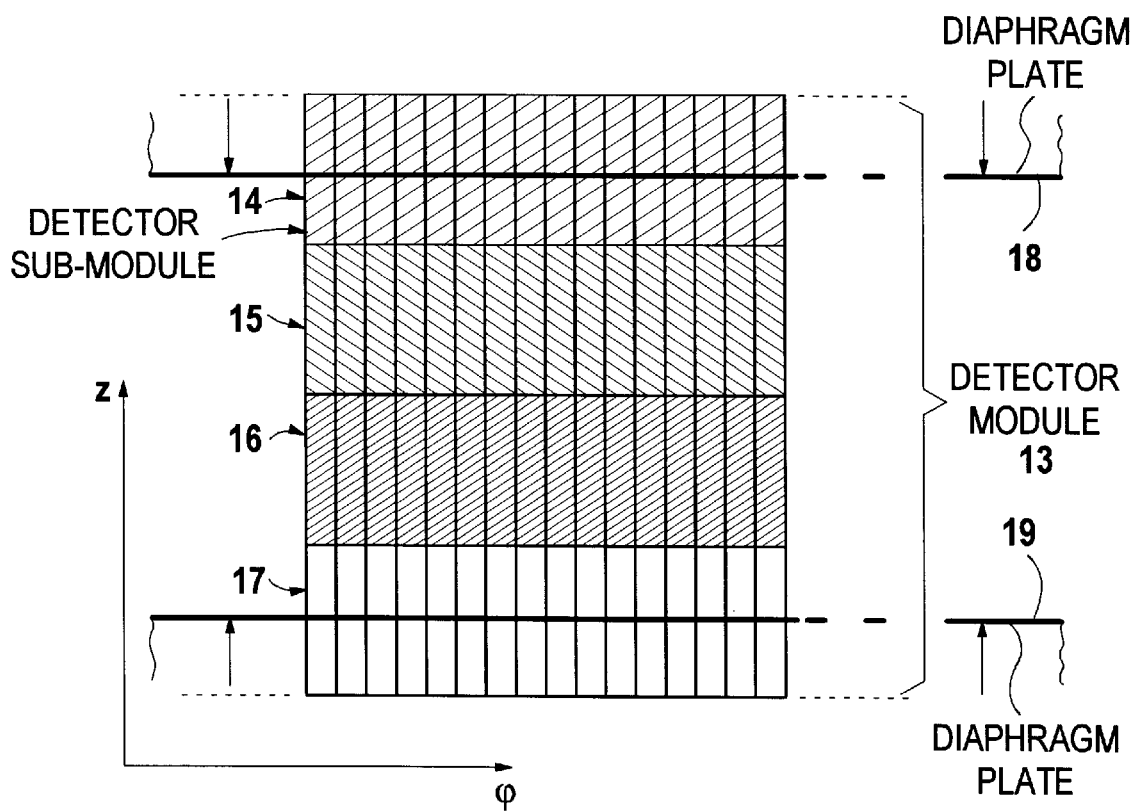

FIG. 6 shows a position of the diaphragm plates 18 and 19 in which the sub-modules 14 and 17 are partly covered. The signals of detector elements corresponding to one another in the respective sub-modules 14 and 15 are combined, and the same is done for corresponding detector elements in the sub-modules 16 and 17. By this means, two parallel slices are scanned simultaneously that are e.g. respectively 8 mm thick (in the z-direction).

The four-row system described above permits the calculation of four images per rotation, which either correspond to the set slice thickness, or can be synthesized into images of correspondingly larger slice thicknesses. In general, slices of N*M mm thickness can be scanned simultaneously (N=no. of rows, M=thickness of individual detector element).

Any known type of X-ray absorbing material can be used for the detector elements, such as e.g. GOS, $CdW_{O4}$, CdTe, GaAs. GOS is particularly suitable, due to ease of manufacture.

The detector can be constructed in modular fashion. The same detector arrangement can be used as a detector with dimensions 2*10 mm as a 4*5 mm detector as in FIG. 3. Cost savings are thus achieved since, for example, only one multiplexer 9 needs to be provided. Cost savings are also achieved in the manufacturing process. The N-row detector system described herein can serve as a basic module for expensive measurement systems with several fan beams.

Although modifications and changes may be suggested by those skilled in the art, it is the intention of the inventor to embody within the patent warranted hereon all changes and modifications as reasonably and properly come within the scope of his contribution to the art.

I claim as my invention:

1. A computed tomography apparatus comprising:

an X-ray source which emits a fan-shaped bundle of X-ray beams;

a radiation detector struck by said X-ray beams;

means for conducting a spiral scan of an examination subject by rotating said X-ray source and said detector around said subject combined with relative longitudinal movement between said examination subject, and said X-ray source and detector;

said detector producing electrical signals corresponding to X-rays incident thereon;

said detector comprising a plurality of modules, each module comprising a plurality of parallel sub-modules, and each sub-module forming only one row of a plurality of detector elements; and means for selectively respectively activating said sub-modules to set a thickness of a slice of said examination subject for which said electrical signals are produced during said spiral scan and for generating an image of said slice of said examination subject from said electrical signals.

2. A computed tomography apparatus as claimed in claim 1 wherein each of said modules consists of two parallel sub-modules.

3. A computed tomography apparatus as claimed in claim 1 wherein each of said modules consists of four parallel sub-modules.

4. A computed tomography apparatus as claimed in claim 1 further comprising diaphragm plates disposed adjacent said detector and means for positioning said diaphragm plates for setting a thickness of said fan-shaped bundle of X-ray beams.

5. A computed tomography apparatus as claimed in claim 4 wherein said means for activating comprises means for selecting a number of parallel slices for simultaneously generating said electrical signals during said spiral scan.

6. A computed tomography apparatus as claimed in claim 1 wherein each detector element comprises a ceramic scintillator and a photodetector electrically connected thereto, and wherein said detector comprises a base of ceramic scintillator material divided by slits to form said detector elements.

* * * * *